US006291731B1

(12) United States Patent
Stamm et al.

(10) Patent No.: US 6,291,731 B1
(45) Date of Patent: Sep. 18, 2001

(54) CONTINUOUS METHOD FOR PRODUCING PROPARGYL CHLORIDE

(75) Inventors: Armin Stamm, Mainz; Jochem Henkelmann, Mannheim; Hans-Jürgen Weyer, Bobenheim-Roxheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,171

(22) PCT Filed: Mar. 8, 1999

(86) PCT No.: PCT/EP99/01462

§ 371 Date: Aug. 29, 2000

§ 102(e) Date: Aug. 29, 2000

(87) PCT Pub. No.: WO99/46226

PCT Pub. Date: Sep. 16, 1999

(30) Foreign Application Priority Data

Mar. 9, 1998 (DE) ................................. 198 10 034

(51) Int. Cl.[7] ..................................... C07C 17/02

(52) U.S. Cl. ............................................................. 570/217
(58) Field of Search ............................... 570/217

(56) References Cited

U.S. PATENT DOCUMENTS 5,196,611  3/1993  Henkelmann et al. .
5,723,704  3/1998  Demail et al. .

FOREIGN PATENT DOCUMENTS

1135893  * 5/1961  (DE) ...................................... 570/217
38 40 340    5/1990  (DE) .
514 683     11/1992  (EP) .
645 357      3/1995  (EP) .
786 442      7/1997  (EP) .

* cited by examiner

*Primary Examiner*—Alan Siegel
(74) *Attorney, Agent, or Firm*—Keil & Weinkauf

(57) ABSTRACT

In a continuous process for preparing propargyl chloride by reacting propargyl alcohol with a chlorinating agent in the presence of a catalyst, the chlorinating agent, propargyl alcohol and from 0.1 to 10 mol % of the catalyst, based on the amount of propargyl alcohol, are continuously metered into a reaction zone and reacted at from 40 to 70° C.

10 Claims, No Drawings

CONTINUOUS METHOD FOR PRODUCING PROPARGYL CHLORIDE

The present invention relates to a continuous process for preparing propargyl chloride by reacting propargyl alcohol with a chlorinating agent in the presence of a catalyst.

Propargyl chloride (3-chloropropyne) is a valuable intermediate which is required for preparing a series of intermediates and electrolysis auxiliaries, but also as a reagent for introducing a propargyl radical in the preparation of active compounds for pharmaceuticals and crop protection.

Numerous methods of preparing propargyl chloride batchwise from propargyl alcohol (propyne-3-ol) are known. On an industrial scale, the most useful are reaction with thionyl chloride ($SOCl_2$) or phosgene ($COCl_2$) since the accompanying products formed are only gaseous products ($SO_2$ or $CO_2$) which spontaneously vaporize from the reaction mixture. Phosgene is particularly preferred since the $CO_2$ formed is less toxic and less environmentally harmful than $SO_2$. The reaction of alkyls with phosgene to form the alcohol chloride requires the use of catalysts.

EP-A-0 786 442 describes a batchwise 2-stage process for preparing alkyl chlorides using phosgene, in which hexaalkylguanidinium halides, substituted ammonium chlorides, phosphonium halides or alkylpyridines are used as catalysts. Reaction of the alcohol with hydrogen chloride is followed by a reaction with phosgene in the presence of the catalyst. The temperature in the reaction is from 120 to 140° C.

DE-A-38 40 340 describes a process for preparing alkyl chlorides in which the alcohol and phosgene are first reacted to give the chloroformate which is subsequently decarboxylated after addition of a catalyst to form the alkyl chloride. The decarboxylation is carried out in the presence of quaternary ammonium or phosphonium salts or ternary sulfonium salts as catalyst.

According to EP-A-0 514 683, alkyl chlorides are prepared from the corresponding alcohols by reaction with phosgene or thionyl chloride in the presence of an aliphatic or cycloaliphatic phosphine oxide as catalyst. The reaction is carried out at from 84 to 100° C.

EP-A-0 645 357 describes a process for preparing secondary alkyl chlorides from the corresponding alcohols, in which the hydrochloride of dimethylformamide is first prepared by passing in hydrogen chloride. Phosgene is then metered in to form a catalyst adduct. The catalyst which has been loaded in this way is reacted with equimolar amounts of alcohol and phosgene. The catalyst is subsequently separated off and loaded again.

The known processes have a series of disadvantages, particularly in the preparation of propargyl chloride. The 2-stage process of EP-A-0 786 442 is complicated to carry out. The decarboxylation of DE-A 38 40 340 is, particularly in the case of industrial production amounts, problematical for safety reasons. For propargyl chloride, a reaction in the high temperature range indicated in EP-A-0 514 683 is associated with safety risks because of its ability to deflagrate owing to the high energy content. The process described in EP-A-0 645 357 requires the presence of large amounts of loaded catalyst. The loading of the catalyst also forms large amounts of hydrochloric acid which, after formation of the propargyl chloride, can undergo an addition reaction with the latter to form dichloropropenes.

For active compounds for pharmaceuticals and crop protection, propargyl chloride is required in high purity and, in particular, with a very low content of 1,3- and 2,3-dichloropropene, since these by-products are very difficult to separate from propargyl chloride by distillation and adversely affect the purity of the active compounds prepared. In addition, dichloropropenes formed have to be subjected to costly disposal if they are separated off.

It is an object of the present invention to provide a process for preparing propargyl chloride by reacting propargyl alcohol with a chlorinating agent in the presence of a catalyst, which avoids the disadvantages of the known processes and gives propargyl chloride in high yields, with the proportion of dichloropropenes in the reaction product being greatly reduced. Preferably, the proportion of dichloropropenes, based on the amounts of propargyl chloride obtained, should be less than 0.2% by weight.

We have found that this object is achieved by a continuous process in which chlorinating agent, propargyl alcohol and from 0.1 to 10 mol % of the catalyst, based on the amount of propargyl alcohol, are continuously metered into a reaction zone and reacted at from 40 to 70° C.

The process of the present invention allows propargyl chloride to be prepared in high purity, with the proportion of dichloropropenes formed as by-product being less than 0.2% by weight. Since, for safety reasons, propargyl chloride is usually no longer purified by distillation, the reduction in the by-product content also considerably improves the product quality.

The amount of catalyst is selected such that the simultaneous formation of propargyl chloroformate during the reaction is suppressed. The chloroformates can react spontaneously with elimination of carbon dioxide to form the chloride. Since the decarboxylation occurs with considerable release of energy and often uncontrollable foaming of the reaction solution, the reaction is carried out such that uniform and complete chlorination occurs without chloroformate formation. This is achieved by adhering to the above reaction conditions, in particular the indicated amount of catalyst and the indicated reaction temperature.

The catalyst is preferably present in an amount of from 1 to 5 mol % and particularly preferably from 2 to 3.5 mol %, based on the amount of propargyl alcohol.

The reaction temperature is preferably in the range from 50 to 60° C.

In this reaction, it is possible to use any suitable chlorinating agent. Examples of suitable chlorinating agents are phosgene and thionyl chloride. Preference is given to using phosgene as chlorinating agent.

As catalyst for the reaction, it is possible to use all suitable catalysts. The catalyst is preferably selected from the group consisting of phosphine oxides, guanidinium salts, open-chain and cyclic alkylureas, alkylacetamides and N,N-dialkylformamides and also mixtures thereof.

The catalyst is particularly preferably at least one formamide of the formula I

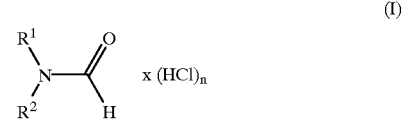

(I)

where $R^1$ and $R^2$ are, independently of one another, straight-chain or branched $C_1$–$C_8$-, preferably $C_2$–$C_6$-, particularly preferably $C_3$–$C_5$-alkyl radicals or together form a straight-chain $C_4$–$C_5$-alkylene radical, each of which may be interrupted by from 1 to 4, preferably 1 or 2, oxygen or nitrogen atoms, and n has a mean value of from 0 to 3, preferably from 0.5 to 2.5, in particular from 1 to 2.

n can represent a mean for the catalyst used. If the HCl content is precisely defined, n is preferably an integer from 0 to 3.

In general, the pure formamide is introduced into the reaction mixture in which the HCl adduct is formed during the phosgenation.

$R^1$ and $R^2$ are preferably the above-described straight-chain or branched $C_1$–$C_8$-alkyl radicals. $R^1$ and $R^2$ are particularly preferably identical radicals selected from among n-butyl and isobutyl.

Particular preference is given to using diisobutylformamide as catalyst.

The reaction can be carried out in the presence of an inert diluent. The diluent is preferably used in an amount of from 10 to 50% by weight, particularly preferably from 20 to 40% by weight, in particular from 20 to 30% by weight, based on the amount of propargyl alcohol used. The diluent used is preferably a substituted aromatic hydrocarbon or a corresponding hydrocarbon mixture. Particularly preferred examples are toluene and xylene isomer mixtures and also mixtures thereof.

The reaction can be carried out in any suitable reaction zone. It is preferably carried out in an apparatus which has a main reactor and a downstream after-reactor which is provided with a stripping column for stripping unreacted chlorinating agent and possibly propargyl chloride. The reactants are metered into the main reactor, the product is discharged from the after-reactor and the stripped-out chlorinating agent and any propargyl chloride is/are condensed and returned to the main reactor and/or after-reactor. The phosgene is fed into the reaction mixture in gaseous or liquid form. The temperature in the main reactor and in the after-reactor is held in the range specified above. The discharged product is generally used for further reactions without further purification.

The continuous process of the present invention enables the content of dichloropropenes, in particular 1,3- and 2,3-dichloropropene, in the reaction product to be reduced to less than 0.2% by area, as determined by GC.

Not only is the dichloropropenes content reduced, but the color of the reaction product is also considerably lightened compared to known processes. The reduced proportion of color-producing components is advantageous for subsequent reactions, since the reaction product is generally not worked up further.

The invention is illustrated by the examples below.

EXAMPLES

The continuous syntheses were carried out in an apparatus comprising a main reactor and an after-reactor and also a stripping column. Excess phosgene was discharged from the main reactor, condensed and returned to the reaction. The stripping column was followed by a condenser which condensed phosgene and stripped-out propargyl chloride which were together returned to the after-reactor.

Example 1

An initial charge of 205 g of propargyl chloride and 80 g of toluene was placed in the apparatus and 0.67 mol/h (37.5 g/h) o1f propargyl alcohol, 23.3 g/h of toluene and 0.023 mol/h (3.6 g/h) of isobutylformamide (3.5 mol %) were metered into the initial charge in such a way that the reaction temperature in the main reactor and after-reactor could be held at 50° C. The reaction was carried out for a total of 24.5 hours. The reaction product taken off after from 17.5 to 24.5 hours comprised, after distillation, 60.1% of propargyl chloride (321 g) and, as determined by means of GC, 0.12% by area of 1,3-dichloropropene and 0.05% by area of 2,3-dichloropropene. The product contained neither propargyl chloroformate nor unreacted propargyl alcohol.

Example 2

0.67 mol/h (37.5 g/h) of propargyl alcohol, 23.3 g/h of toluene and 0.0134 mol/h (2.1 g/h) of diisobutylformamide (=2 mol %) are metered into an initial charge composed of the reaction product from Example 1 in such a way that the reaction temperature in the main reactor and secondary reactor can be held at 50° C. The reaction proceeds for a total of 19.5 hours. The reaction product comprises, according to GC analysis, 63% of propargyl chloride, 0.10% of 1,3-dichloropropene and 0.04% of 2,3-dichloropropene, no chloroformate and no unreacted propargyl alcohol.

Example 3

1 mol/h (56 g/h) of propargyl alcohol, 35 g/h of toluene and 0.0198 mol/h (3.1 g/h) of diisobutylformamide (=2 mol %) are metered into the reaction product from Example 2 in such a way that the reaction temperature in the main reactor and the secondary reactor can be held at 50° C. The reaction proceeds for a total of 10 hours. The reaction product comprises, according to GC analysis, 65% of propargyl chloride, 0.06% of 1,3-dichloropropene and 0.03% of 2,3-dichloropropene, no chloroformate and no unreacted propargyl alcohol.

Example 4

1.25 mol/h (70 g/h) of propargyl alcohol, 43.7 g/h of toluene and 0.025 mol/h (3.9 g/h) of diisobutylformamide (=2 mol %) are metered into the reaction product from Example 3 in such a way that the reaction temperature in the main reactor and the secondary reactor can be held at 50° C. The reaction proceeds for a total of 7 hours. The reaction product comprises, according to GC analysis, 65% of propargyl chloride, 0.05% of 1,3-dichloropropene and 0.02% of 2,3-dichloropropene, no chloroformate and no unreacted propargyl alcohol.

Example 5

22 g of diisobutylforamide (0.14 mol, 7 mol %) are initially charged in 70 g of toluene. At a constant temperature of 50° C., 112 g of propargyl alcohol (2 mol) and 230 g of phosgene (2.3 mol) are fed in over a period of 3.5 hours. After an after-reaction time of 1 hour at 50° C., further propargyl alcohol is added to react with excess phosgene. After a further after-reaction time of 1 hour, the reaction product comprises, according to GC analysis, 65% of propargyl chloride, 0.18% of 1,3-dichloropropene and 0.07% of 2,3-dichloropropene.

We claim:

1. A continuous process for preparing propargyl chloride which comprises reacting a propargyl alcohol with a chlorinating agent in the presence of at least one formamide of the formula I

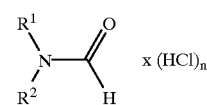

where $R^1$ and $R^2$ are, independently of one another, straight-chain or branched $C_1$–$C_8$-alkyl radicals or together form a straight-chain $C_4$–$C_5$-alkylene radical, each of which may be interrupted by from 1 to 4 oxygen or nitrogen atoms, and n has a mean value in the range from 0 to 3, as catalyst, wherein the chlorinating agent, propargyl alcohol and from 0.1 to 10 mol % of the catalyst, based on the amount of propargyl alcohol, are continuously metered into a reaction zone and reacted at from 40 to 70° C.

2. The process of claim 1, wherein the chlorinating agent used is phosgene.

3. The process of claim 1, wherein the reaction is carried out in the presence of from 10 to 50% by weight, based on the amount of propargyl alcohol used, of an inert diluent.

4. The process of claim 3, wherein the diluent used is a substituted aromatic hydrocarbon.

5. The process of claim 1, wherein the reaction is carried out in an apparatus which has a main reactor and a downstream after-reactor which is provided with a stripping column for stripping unreacted chlorinating agent and possibly propargyl chloride, where the reactants are metered into the main reactor, the product is discharged from the after-reactor and the stripped-out chlorinating agent and any propargyl chloride is/are condensed and returned to the main reactor and/or after-reactor.

6. The process of claim 1, wherein the catalyst is used in an amount of from 1 to 5 mol %, based on the amount of propargyl alcohol.

7. The process of claim 1, wherein the reaction is carried out at from 50 to 60° C.

8. The process of claim 1, wherein n has a mean value of from 0.5 to 2.5.

9. The process of claim 1, wherein n has a mean value of from 1 to 2.

10. The process of claim 1, wherein n is an integer from 1 to 3.

* * * * *